United States Patent

Okada et al.

[11] Patent Number: 5,916,881
[45] Date of Patent: Jun. 29, 1999

[54] HIGH TREHALOSE CONTENT SYRUP

[75] Inventors: Katsuhide Okada; Takashi Shibuya; Toshio Miyake, all of Okayama, Japan

[73] Assignee: Kabushiki Kaisha Hayashibara Seibutsu Kagaku Kenkyujo, Okayama, Japan

[21] Appl. No.: 08/942,266

[22] Filed: Oct. 1, 1997

[30] Foreign Application Priority Data

Oct. 7, 1996 [JP] Japan ..................... 8-300786

[51] Int. Cl.⁶ .................. A61K 31/70; A61K 31/715; A23G 3/00; C12P 19/14
[52] U.S. Cl. ..................... 514/53; 426/658; 435/99; 435/100; 435/101; 514/54; 514/61; 536/123.1; 536/123.13
[58] Field of Search .................. 514/53, 54; 536/123.1, 536/123.13, 61; 426/658; 435/99, 100, 101

[56] References Cited

U.S. PATENT DOCUMENTS

| | | | |
|---|---|---|---|
| 5,576,303 | 11/1996 | Takashi et al. | 514/53 |
| 5,604,211 | 2/1997 | Chaen et al. | 514/53 |
| 5,681,826 | 10/1997 | Takashi et al. | 514/54 |

FOREIGN PATENT DOCUMENTS

| | | |
|---|---|---|
| 0289138 | 11/1988 | European Pat. Off. . |
| 662479 | 7/1995 | European Pat. Off. . |
| 0691344 | 1/1996 | European Pat. Off. . |
| 739986 | 10/1996 | European Pat. Off. . |
| 0154485 | 12/1975 | Japan . |
| 8216695 | 12/1983 | Japan . |
| 450319 | 8/1992 | Japan . |
| 7143876 | 6/1995 | Japan . |
| 7170977 | 7/1995 | Japan . |
| 7213283 | 8/1995 | Japan . |
| 789916 | 10/1995 | Japan . |
| 8217784 | 8/1996 | Japan . |

OTHER PUBLICATIONS

S. Kobayashi, "Food Chemicals", vol. 8, No. 88, pp. 67–72, Aug., 1992.
Denpunto–Gijutsu–Bukai, "Denpunto–Kanren–Kogyo–Bunsekiho", 1991.
G.G. Birch, "Trehaloses", Advances in Carbohydrate Chemistry, vol. 18, pp. 201–225, 1963.
I. Hoelzle et al., "Increased Accumulation of Trehalose in Rhizobia Cultured Under 1% Oxygen", Applied and Environmental Microbiology, vol. 56, No. 10, pp. 3213–3215, Oct., 1990.

*Primary Examiner*—Howard C. Lee
*Attorney, Agent, or Firm*—Browdy and Neimark

[57] ABSTRACT

A non- or substantially non-crystalline high trehalose content syrup, which dissolves trehalose in an amount over the water solubility and dissolves other oligosaccharide having a trehalose structure within the molecule. The oligosaccharide acts as a trehalose crystallization inhibitory agent and makes the syrup stable, free of or substantially free of crystallization at ambient temperature, and free from bacterial contamination. Examples of the oligosaccharide are monoglucosyltrehalose, diglucosyltrehalose, and triglucosyltrehalose.

21 Claims, No Drawings

HIGH TREHALOSE CONTENT SYRUP

BACKGROUND OF THE INVENTION

1. Field of the Invention

The present invention relates to a stabilized syrup with the highest possible amount of trehalose, more particularly, to a non- or substantially non-crystalline high trehalose content syrup which dissolves trehalose in an amount over the water solubility and dissolves other oligosaccharide having a trehalose structure within the molecule, and uses thereof, as well as to a method for preventing the crystallization of trehalose in high trehalose content syrups, an agent for preventing the crystallization of trehalose syrups which contains as an effective ingredient at least one oligosaccharide having a trehalose structure within the molecule, and a process for producing the syrups.

2. Description of the Prior Art

Trehalose or α, α-trehalose has long been known as a non-reducing saccharide consisting of glucose molecules. As described in "Advances in Carbohydrate Chemistry", Vol.18, pp.201–225 (1963), published by Academic Press, USA, and "Applied and Environmental Microbiology", Vol 56, pp.3,213–3,215 (1990), trehalose widely exists in microorganisms, mushrooms, insects, etc., though the content is relatively low. Since non-reducing saccharides including trehalose do not react with amino group-containing substances such as amino acids and proteins, they neither induce the amino-carbonyl reaction nor affect the substances. Thus, non-reducing saccharides have been believed to be used without fear of causing unsatisfactory browning and deterioration. Because of these, it has been in great demand to establish preparations of such non-reducing saccharides.

In conventional preparations of trehalose, as disclosed in Japanese Patent Kokai No.154,485/75, microorganisms are used or as proposed in Japanese Patent Kokai No.216,695/83, maltose is converted into trehalose by using maltose- and trehalose-phosphorylases in combination. The former, however, is not suitably used on industrial-scale preparations because the content of trehalose present in the microorganisms as starting material is usually less than 15 w/w % (the wording "w/w %" will be abbreviated as "%" in the specification, if not specified otherwise), on a dry solid basis (d.s.b.) and the extraction and purification steps used are complicated. The latter has the following demerits: Since trehalose is formed via glucose-1-phosphate, (i) maltose as a substrate could not be used at a relatively-high concentration; (ii) the enzymatic reaction systems of the phosphorylases are reversible reactions, and the yield of the desired trehalose is relatively low; and (iii) it is substantially difficult to keep their reaction systems stably and to continue their enzymatic reactions smoothly. Thus, no such a method has been realized as an industrial-scale preparation.

As regards the preparation of trehalose, it is reported in the column titled "Oligosaccharides" in the chapter titled "Current Status of Starch Application Development and Related Problems" in "Food Chemicals", No.88, pp.67–72 (August, 1992) that "In spite of a wide applicability of trehalose, an enzymatic preparation thereof via a direct saccharide-transfer reaction or a hydrolytic reaction has been reported to be scientifically almost impossible in this field." Thus, an enzymatic preparation of trehalose from material starches has been believed to be scientifically very difficult.

It is known that partial starch hydrolysates prepared from starches as materials such as liquefied starches, cyclodextrins, and maltooligosaccharides usually contain reducing end-groups as end units. These partial starch hydrolysates are referred to as "reducing partial starch hydrolysates" in the specification. The reducing power of such reducing partial starch hydrolysates is generally expressed by "Dextrose Equivalent (DE) value", based on their dry solid. It is known that among reducing partial starch hydrolysates those with a relatively-high DE generally have a lower molecular weight and viscosity, as well as a relatively-high level of sweetness and reactivity, and easily react with substances having amino groups such as amino acids and proteins to cause unsatisfiable browning, smell, and deterioration of their quality.

These properties of reducing partial starch hydrolysates are varied depending on their DE values, and the relationship between reducing partial starch hydrolysates and their DE values is very important. It has been even believed to be impossible to break off the relationship in this field.

The only way to break off the relationship is to form non-reducing saccharides from reducing partial starch hydrolysates by hydrogenating the hydrolysates at a relatively-high hydrogen pressure to convert their reducing end-groups into hydroxyl groups. The method, however, requires a considerably-high-pressure autoclave, consumes excessive amounts of hydrogen and energy, and also requires a relatively-high level of control or safety facility to prevent disasters. The material reducing partial starch hydrolysates and the resultant products differ because the former consists of glucose units and the latter, i.e., sugar alcohols of the resultant partial starch hydrolysates, consists of glucose and sorbitol units which may cause symptoms such as digestive disorder and diarrhea when administered to the body. Thus, it has been in great demand to establish a method to decrease or even eliminate the reducing power of reducing partial starch hydrolysates without changing the chemical structure of glucose as a constituent saccharide thereof.

To overcome these problems, the present applicant, as disclosed in Japanese Patent Kokai No.143,876/95, disclosed a novel non-reducing saccharide-forming enzyme which forms non-reducing saccharides having a trehalose structure as an end unit from one or more reducing partial starch hydrolysates with a glucose polymerization degree of at least 3, and established a method for producing non-reducing saccharides with a trehalose structure as an end unit and a glucose polymerization degree of at least 3 and a method for producing trehalose from the non-reducing saccharides.

As disclosed in Japanese Patent Kokai No.213,283/95, the present applicant disclosed a novel trehalose-releasing enzyme which specifically hydrolyzes the bonding between a trehalose moiety and other moiety in non-reducing saccharides with a trehalose structure as an end unit and a glucose polymerization degree of at least 3 (the enzyme is designated as "trehalose-releasing enzyme" in the specification, hereinafter) and a method for producing trehalose in a relatively-high yield by using the above non-reducing saccharide-forming enzyme and the trehalose-releasing enzyme. The applicant also disclosed in Japanese Patent Kokai No.170,977/95 a maltose/trehalose converting enzyme which directly converts maltose into trehalose from reducing partial starch hydrolysates.

Thereafter, during the study of the uses of trehalose, the present applicant found that besides powdery crystalline products such as hydrous- and anhydrous-crystalline trehalose, much more required is a high trehalose content syrup which can be tank-stored, pump-transported, transported by tank trucks, and easily handled. However, it was found that trehalose has a relatively-low water solubility and an unsaturated trehalose solution has a relatively-low concentration, and this easily allow bacteria to grow and results in bacterial contamination, while a saturated trehalose solution is highly-unstable at ambient temperature and this easily causes trehalose to crystallize into crystalline trehalose hydrate and to easily lose its homogeneous fluidity as a feature of trehalose syrups, resulting in serious affects on tank-storage and pump-transportation. In view of these, stable trehalose syrups with the highest possible amount of trehalose have been required.

To solve the aforesaid drawbacks, the present applicant studied and found that, as disclosed in Japanese Patent Application Nos.110,291/95 and 112,159/96, syrups which dissolve trehalose over the water solubility and dissolve other saccharides, preferably, those which dissolve trehalose over the water solubility and other saccharides in an amount of not lower than the amount of trehalose, more preferably, those which dissolve 18.5–25.0% trehalose and other saccharides in an amount of not lower than the amount of trehalose and contain 25–35 w/w % moisture are stable at ambient temperature and agreeable to the object of the present invention. After further studying, it was found that the above high trehalose content syrups, however, are defective in their insufficient trehalose content and a relatively-high DE as a whole. Therefore, highly required are high trehalose content syrups which have a lower DE and a satisfactory stability at ambient temperature

SUMMARY OF THE INVENTION

The present invention provides (i) a high trehalose content syrup which has an increased trehalose content, does not or substantially does not crystallize at ambient temperature, has a satisfactory stability, and does not substantially have bacterial contamination, (ii) uses of the syrup, (iii) a method for preventing the crystallization of trehalose in a high trehalose content syrup with more increased trehalose content, and (iv) a process for producing the syrup.

DETAILED DESCRIPTION OF THE INVENTION

The present indentors studied methods for preventing the crystallization of trehalose to solve the above object and continued studying to establish a trehalose syrup with a satisfactory stability at ambient temperature, which dissolves trehalose in a relatively-high concentration, preferably, in a concentration exceeding 25 w/w % to the syrup. As a result, the present inventors found that oligosaccharides having a trehalose structure within the molecules specifically and effectively prevent the crystallization of trehalose, and accomplished this indention: According to the present invention, the existence of the oligosaccharides provide a stabilized high trehalose content syrup at ambient temperature which dissolves trehalose in an amount that exceeds the water solubility, i.e., up to a level of about 2.8-times the water solubility. Preferable content of the oligosaccharides to be incorporated is at least 10% to the trehalose, d.s.b., and more preferable content of water is not higher than 35 w/w % to prevent bacterial contamination.

The high trehalose content syrup, which dissolves trehalose in an amount that exceeds the water solubility and dissolves other oligosaccharides having a trehalose structure within their molecules, includes supersaturated trehalose solutions at ambient temperature, preferably, those which dissolve trehalose up to a level of about 2.8-times the water solubility, more preferably, up to a level of 1.3–2.8 times, preferably, those which have a water content of not higher than about 35 w/w %, more preferably, about 25–35 w/w %, and dissolve at least 10% other oligosaccharides to the trehalose, d.s.b., and which are non- or substantially non-crystalline syrups at ambient temperature. Any preparation can be used in the present invention as long as it produces the above syrups; for example, such syrups can be prepared either by dissolving by heating trehalose in water in an amount that exceeds the water solubility, then incorporating other oligosaccharides having a trehalose structure within the molecules in the aqueous trehalose solutions, or by mixing the above supersaturated solutions with high-concentration solutions of other oligosaccharides having a trehalose structure within the molecule to meet their purposes.

The water content of the present high trehalose content syrup can be easily measured, for example, by the sand mixing drying method as disclosed in "*Denpunto-Kanren-Kogyo-Bunsekiho*", edited by *Denpunto-Gijutsu-Bukai*, published by *Kabushiki-Gaisha-Shokuhin-Kagaku-Shinbunsha*, Tokyo, Japan (1991).

The trehalose used in the present invention is not restricted to specific preparations. Crystalline trehalose hydrate can be advantageously used in the present invention. In general, relatively low purity, low cost trehalose products containing other saccharides as impurities can be satisfactorily used than relatively high purity, high cost trehalose products. Examples of such low purity, low cost trehalose products include syrups containing trehalose prepared by contacting non-reducing saccharide-forming enzymes or trehalose-releasing enzymes with reducing partial starch hydrolysates, as disclosed in Japanese Patent Kokai Nos.143,876/95 and 213,283/95 applied by the present applicant, and those prepared by contacting maltose/trehalose converting enzymes with maltose as disclosed in Japanese Patent Kokai No.170,977/95. Mother massecuites, obtained by concentrating and crystallizing the syrups into massecuites with crystalline trehalose hydrate, can be included in such examples. Generally, the resulting trehalose solutions contain about 40–80% trehalose, d.s.b., and they can be arbitrarily used in the present invention as material syrups.

Examples of other oligosaccharides having a trehalose structure within their molecules include monoglucosyltrehaloses such as α-glucosyltrehalose and α-isomaltosyl-α-glucoside, diglucosyltrehaloses such as α-maltosyltrehalose, α-maltosyl-α-maltose, α-isomaltosyl-α-maltoside and α-isomaltosyl-α-isomaltoside, and triglucosyltrehaloses such as α-maltosyl-α-maltotrioside and α-maltotriosyltrehalose. These oligosaccharides can be arbitrarily used as effective ingredients in agent for preventing crystallization of trehalose.

The crystallization inhibitory effect on trehalose can be exerted by coexisting in trehalose syrups one or more other oligosaccharides having a trehalose structure within their molecules in an amount of at least 10%, preferably, at least 30% oligosaccharides to the trehalose, d.s.b. More particularly, diglucosyltrehaloses are most satisfactorily used because they exert a strong effect. If necessary, one or more other saccharides such as mono-, di- and higher-saccharides can be arbitrarily used to practice the present method for preventing the crystallization of trehalose.

It can arbitrarily produced from starches directly the present high trehalose content syrup which dissolves a prescribed amount of trehalose and other oligosaccharides having a trehalose structure within their molecules. Examples of such preparations are as follows: In accordance with the method as disclosed in Japanese Patent Kokai No.213,283/95 applied by the present applicant, contact starch suspensions with concentrations of 10% or more with acids or α-amylases into liquefied solutions with a DE of 5 or less, contact the solutions with starch debranching enzymes, non-reducing saccharide-forming enzymes and trehalose-releasing enzymes to produce products with about 40–60% trehalose, d.s.b., contact the products with one or more enzymes selected from α-amylases, β-amylases, cyclomaltodextrin glucanotransferases, etc., and treat in a conventional manner the resulting mixtures with heat to inactivate the remaining enzymes, decoloration using activated charcoals, and desalting and purification using ion exchangers in H- and OH-form. If necessary, the solutions thus obtained can be treated with column chromatography using a strong-acid cation exchanger as disclosed in Japanese Patent Kokoku No.50,319/92 to remove monosaccharides as impurities to increase the content of the desired saccharides, followed by concentrating the resulting solutions until obtaining high trehalose content syrups having a moisture content of about 35 w/w % or less and dissolving trehalose in an amount that exceeds the water solubility and dissolving other oligosaccharides having a trehalose structure within their molecules.

For the production of the present high trehalose content syrup using maltotetraose-forming enzymes, for example, in accordance with the method in Japanese Patent Kokai No.143,876/95 applied by the present applicant, the present syrup can be produced by contacting high maltotetraose content solutions with non-reducing saccharide-forming enzymes to form about 30–60% maltosyltrehalose, d.s.b., contacting the maltosyltrehalose with one or more enzymes selected from α-amylase, β-amylase, maltose-forming amylase, cyclomaltodextrin glucanotransferase, etc., and, according to the above method, purifying and concentrating the resulting solutions into high trehalose content syrups having a moisture content of about 35% or less and dissolving trehalose in an amount that exceeds the water solubility and dissolving other oligosaccharides having a trehalose structure within their molecules.

The high trehalose content syrups thus obtained are free from or substantially free from crystallization and easily handled even when allowed to stand at temperatures of 15° C. or less. The syrups have (i) a DE lower than that of conventional starch saccharides, preferably, a DE of less than 20, (ii) a relatively-lower reducibility, and (iii) a relatively-higher stability, and (iv) do not change their qualities and substantially do not deteriorate ingredients such as vitamins and amino acid-containing substances such as amino acids, oligopeptides, and proteins even when mixed and processed with such ingredients. Because of these, the syrups can be arbitrarily used as syrups with a relatively-low viscosity and sweetness in food products, cosmetics, and pharmaceuticals. The syrups can be treated with high-pressure hydrogenation to diminish their reducibility on demand.

The present high trehalose content syrup is easily decomposed by trehalase in vivo into glucose, and other oligosaccharides having a trehalose structure, contained in the syrup, are easily decomposed by α-glucosidase and intestinal enzymes into glucose and trehalose. The formed trehalose is then easily decomposed into glucose. Thus, the syrup is orally administrable, assimilated, adsorbed, and used by living bodies as calorie and energy sources. The syrup can be also used as a sweetener which substantially does not induce dental caries because it is scarcely fermented by dental-caries-inducing microorganisms.

The present high trehalose content syrup can be boiled up into high-quality hard candies with no trehalose crystal. As satisfactory properties, the syrup has an effective osmosis controllability, formability, gloss-imparting ability, humectancy, viscosity, crystallization-preventing ability for other saccharides, insubstantial fermentability, retrogradation-preventing ability for gelatinized starches, etc.

The high trehalose content syrup according to the present invention can be arbitrarily used as sweeteners, taste-imparting agents, quality-improving agents, stabilizers, diluents, fillers, excipients, bases for pulverization, etc., in food products, cosmetics, pharmaceuticals, etc.

The present high trehalose content syrup can be used intact as a seasoning for sweetening. If necessary, the syrup can be used together with adequate amounts of one or more other sweeteners, for example, powdered syrup, glucose, maltose, sucrose, isomerized sugar, honey, maple sugar, isomaltooligosaccharide, galactooligosaccharide, fructooligosaccharide, lactosucrose, sorbitol, maltitol, lactitol, dihydrocharcone, stevioside, α-glycosyl stevioside, rebaudioside, glycyrrhizin, L-aspartyl-L-phenylalanine methyl ester, saccharin, glycine, and alanine, as well as fillers such as dextrins, starches, and lactose.

The present high trehalose content syrup can be arbitrarily mixed with crystalline trehalose hydrate to improve the quality of products containing crystalline trehalose hydrate. For example, in the case of producing icings, soft candies and bonbons which contain crystalline-trehalose hydrate, the present syrup can be incorporated into the crystalline trehalose hydrate in an amount of not higher than the amount of the trehalose hydrate, preferably, less than 50% to the hydrate to impart an adequate humectancy, formability and adhesiveness to those products and to keep their initial high quality just after their processings for a relatively-long period of time.

The present high trehalose content syrup has a relatively-low viscosity, DE and sweetness, and it can be used as a base for pulverization. Powdery products obtained from the syrup are substantially free of humectancy and satisfactory in heat tolerance, acid tolerance and stability. Because of these, the powdery products can be arbitrarily used intact as a filler, adjuvant, or excipient, and if necessary, they can be mixed with other fillers, adjuvants, excipients, and binders and formed into granules, spheres, shot-rods, plates, cubes, and tablets, prior to their use. The powdery products can be also used, for example, in materials for confectioneries and bakeries by replacing with them partly or wholly amylaceous powders such as wheat flours, corn grits, and starches.

The present high trehalose content syrup has a sweetness which well harmonizes with substances having sourness, acidity, saltiness, bitterness, astringency and deliciousness, and has a satisfactory acid- and heat-tolerance. Thus, they can be arbitrarily used in food products in general as a sweetener, taste-improving agent, and quality-improving agent.

The present high trehalose content syrup can be used in seasonings such as amino acids, peptides, soy sauces, powdered soy sauces, "miso", "funmatsu-miso" (a powdered miso), "moromi" (a refined sake), "hishio" (a refined soy sauce), "furikake" (a seasoned fish meal), mayonnaise, dressings, vinegars, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "ment-suyu" (a sauce for Japanese vermicelli), sauces, catsups, "yakiniku-no-tare" (a sauce for Japanese grilled meat), curry roux, instant stew mixes, instant soup mixes, "dashi-no-moto" (an instant stock mix), nucleic acid condiments, mixed seasonings, "mirin" (a sweet sake), "shin-mirin" (a synthetic mirin), table syrups and coffee syrups.

The present syrup can be freely used for sweetening "wagashi" (Japanese cakes) such as "senbei" (a rice cracker), "arare-mochi" (a rice-cake cube), "okoshi" (a millet-and-rice cake), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jellies, pao de Castellas and "amedama" (a Japanese toffee); confectioneries such as buns, biscuits, crackers, cookie, pies, puddings, butter creams, custard creams, cream puffs, waffles, sponge cakes, doughnuts, chocolates, chewing gums, caramels and candies; frozen desserts such as ice creams and sherbets; syrups such as "kajitsu-no-syrup-zuke" (a preserved fruit) and "korimitsu" (a sugar syrup for shaved ice); pastes such as flour pastes, peanut pastes, fruit pastes and spreads; processed fruits and vegetables such as jams, marmalades, "syrup-zuke" (fruit pickles) and "toka" (conserves); pickles and pickled products such as "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); premixes for pickles and pickled products such as "takuan-zuke-no-moto" (a premix for pickled radish) and "hakusai-zuke-no-moto" (a premix for fresh white rape pickles); meat products such as hams and sausages; products of fish meats such as fish hams, fish sausages, "kamaboko" (a steamed fish paste), "chikuwa" (a kind of fish paste) and "tenpura" (a Japanese deep-fat fried fish paste); "chinmi" (relish) such as "uni-no-shiokara" (salted guts of sea urchin), "ika-no-shiokara" (salted guts of squid), "su-konbu" (processed tangle), "saki-surume" (dried squid strips) and "fugu-no-mirin-boshi" (a dried mirin-seasoned swellfish); "tsukudani" (foods boiled down in soy sauce) such as those of lavers, edible wild plants, dried squids, fishes and shellfishes; daily dishes such as "nimame" (cooked beans), potato salads and "konbu-maki" (a tangle roll); milk products such as yogurt and cheese; canned and bottled products such as those of meats, fish meats, fruits and vegetables; alcoholic beverages such as synthetic sakes, wines and liquors; soft drinks such as coffees, teas, cocoas, juices, carbonated beverages, sour milk beverages and beverages containing lactic acid bacteria; instant food products such as instant pudding mixes, instant hot cake mixes and "sokuseki-shiruco" (an instant mix of adzuki-bean soup with rice cake) and instant soup mixes; and foods such as baby foods, foods for therapy, beverages supplemented with nutritions, peptide foods, frozen foods, cooked rice products, and noodles; as well as for improving the tastes and qualities of the above food products.

The present high trehalose content syrup can be also used in feeds and pet foods for animals such as domestic animals, poultry, honey bees, silk warms and fishes to improve their taste preferences. The present syrup can be arbitrarily used as a sweetener, taste-improving agent, quality-improving agent, and stabilizer in other products in a paste and liquid form such as tobaccos, cigarettes, dentifrices, lipsticks, rouges, lip creams, internal medicines, tablets, troches, cod liver oils in the form of drops, cachous, oral refrigerants, gargles, cosmetics, and pharmaceuticals.

The present high trehalose content syrup can be used as a quality-improving agent and stabilizer in biologically active substances susceptible to lose their effective ingredients and activities, as well as in health foods and pharmaceuticals containing the biologically active substances. Examples of such a biologically active substance are lymphokines such as $\alpha$-, $\beta$- and $\gamma$-interferons, tumor necrosis factor-$\alpha$ (TNF-$\alpha$), tumor necrosis factor-$\beta$ (TNF-$\beta$), macrophage migration inhibitory factor, colony-stimulating factor, transfer factor and interleukin 2; hormones such as insulin, growth hormone, prolactin, erythropoietin and follicle-stimulating hormone; biological preparations such as BCG vaccine, Japanese encephalitis vaccine, measles vaccine, live polio vaccine, smallpox vaccine, tetanus toxoid, Trimeresurus antitoxin and human immunoglobulin; antibiotics such as penicillin, erythromycin, chloramphenicol, tetracycline, streptomycin and kanamycin sulfate; vitamins such as thiamine, riboflavin, L-ascorbic acid, cod liver oil, carotenoid, ergosterol and tocopherol; enzymes such as lipase, elastase, urokinase, protease, $\beta$-amylase, isoamylase, glucanase and lactase; extracts such as ginseng extract, snapping turtle extract, chlorella extract, aloe extract and propolis extract; viable microorganisms such as viruses, lactic acid bacteria and yeasts; and other biologically active substances such as royal jelly. By using the present syrup, the aforementioned biologically active substances are arbitrary prepared into health foods and pharmaceuticals in a liquid, paste, and solid form and with a satisfactorily-high stability and quality without fear of losing or inactivating their effective ingredients and activities.

As described above, methods to incorporate the present high trehalose content syrup into the above compositions include conventional methods, for example, mixing, kneading, dissolving, melting, soaking, permeating, sprinkling, applying, coating, spraying, injecting, crystallizing and solidifying. The present syrup is usually incorporated into the compositions in an amount of 0.5% or more, preferably, one % or more.

The following experiments explain the present invention in more detail:

EXPERIMENT 1

Influence of Ambient Temperature on the Water Solubility of Trehalose

The water solubility of trehalose at ambient temperature was studied by placing in a glass beaker 10 parts by weight of water and 20 parts by weight of crystalline trehalose hydrate, allowing the solution to stand at 5, 10, 15, 20, 25, 30 or 40° C. while stirring, sampling the solution, filtering the sample, and measuring the trehalose content in the filtrate to determine the solubility of trehalose in 100 g water at each temperature, i.e., the amount (g) of trehalose, d.s.b., that dissolves in 100 g water to give a saturated solution at each temperature. The results were in Table 1:

TABLE 1

| Temperature (°C.) | 5 | 10 | 15 | 20 | 25 | 30 | 40 |
|---|---|---|---|---|---|---|---|
| Amount of trehalose (g) dissolving in 100 g water | 49.6 | 55.3 | 61.8 | 68.9 | 77.3 | 86.6 | 109.2 |
| Trehalose concentration (%) | 33.2 | 35.6 | 38.2 | 40.8 | 43.6 | 46.4 | 52.2 |

The results in Table 1 revealed that trehalose is a saccharide that has a relatively-low water solubility and easily crystallizes at ambient temperature.

EXPERIMENT 2

Influence of Coexisting Saccharides on the Trehalose Crystallization Inhibitory Effect of Trehalose Syrup that Dissolves Trehalose Over the Water Solubility Trehalose was dissolved by heating in water in an amount of 1.5-times the water solubility at 10° C., and the trehalose solution was allowed to stand at a relatively-cold place for checking the trehalose crystallization inhibitory effect by saccharides. Based on the results in Experiment 1, 1.5-times the water solubility of trehalose in 100 parts by weight of water at 10° C. corresponded to 83 parts by weight of trehalose anhydride. With this relationship, testing solutions were prepared by dissolving by heating in 100 parts by weight of water in a respective glass beaker 83 parts by weight of trehalose, and a saccharide in an amount of 10% to the trehalose, i.e., 8.3 parts by weight of the saccharide selected from the group consisting of glucose, maltose, isomaltose, lactose, maltotriose, panose, maltotetraose, sorbitol, maltitol, maltotriitol, sucrose, raffinose, erlose, saccharides such as α-glucosyltrehalose or monoglucosyltrehalose, α-maltosyltrehalose or diglucosyltrehalose, and α-maltotriosyltrehalose or triglucosyltrehalose as disclosed in Japanese Patent Kokai No.143,876/95 by the present applicant; a saccharide such as α-isomaltosyl-α-glucoside or monoglucosyltrehalose as disclosed in Japanese Patent Kokai No.217,784/96 by the same applicant; and a saccharide such as α-maltosyl-α-maltoside or diglucosyltrehalose as disclosed in Japanese Patent Application No.167,486/94 by the same applicant. Each solution was allowed to stand in a thermostatic place kept at 5, 10 or 15° C. for one week, followed by macroscopically observing the presence of trehalose crystal for evaluating the trehalose crystallization inhibitory effect by the saccharides. The results were in Table 2:

TABLE 2

| | | Coexisting saccharide (8.3 parts by weight) | Formation of trehalose Crystal* | | |
|---|---|---|---|---|---|
| | | | 5° C. (1.7**) | 10° C. (1.5**) | 15° C. (1.3**) |
| | | Glucose | + | + | + |
| | | Maltose | + | + | + |
| | | Isomaltose | + | + | + |
| | | Lactose | + | + | + |
| | | Maltotriose | + | + | + |
| | | Panose | + | + | + |
| | | Maltotetraose | + | + | + |
| | | Sorbitol | + | + | + |
| X | Y | Maltitol | + | + | + |
| | | Maltotriitol | + | + | + |
| | | Sucrose | + | + | + |
| | | Raffinose | + | + | + |
| | | Erlose | + | + | + |
| | | α-Glycosyltrehalose (Monoglucosyltrehalose) | − | − | − |
| | | α-Isomaltosyl-α-glucoside (Monoglucosyltrehalose) | − | − | − |
| | | α-Maltosyltrehalose (Diglucosyltrehalose) | − | − | − |
| | | α-Maltosyl-α-maltoside (Diglucosyltrehalose) | − | − | − |

TABLE 2-continued

| Coexisting saccharide (8.3 parts by weight) | Formation of trehalose Crystal* | | |
|---|---|---|---|
| | 5° C. (1.7**) | 10° C. (1.5**) | 15° C. (1.3**) |
| α-Maltotriosyltrehalose (Triglucosyltrehalose) | + | + | − |

Note)
"*": "+" means that trehalose crystallized and "−" means that trehalose did not.
"**": Each value means a number to be multiplied with respect to the water solubility of trehalose at each temperature.
"X": It shows 100 parts by weight of water.
"Y": It shows 83 parts by weight of trehalose.

As evident from the results in Table 2, it was revealed that when trehalose was dissolved in an amount over the water solubility, the crystallization of trehalose was specifically and effectively inhibited by dissolving other oligosaccharides having a trehalose structure within their molecules; for example, monoglucosyltrehaloses such as α-glucosyltrehalose and α-isomaltosyl-α-glucoside, diglucosyltrehaloses such as α-maltosyltrehalose and α-maltosyl-α-maltoside, and triglucosyltrehaloses such as α-maltotriosyltrehalose. The α-maltotriosyltrehalose or triglucosyltrehalose had a relatively-low trehalose crystallization inhibitory effect.

EXPERIMENT 3

Influences of the Concentrations of Trehalose and Other Oligosaccharides Having a Trehalose Structure Within their Molecules on the Trehalose Crystallization Inhibitory Effect on Syrups Containing Trehalose Over the Water Solubility The trehalose crystallization inhibitory effect was experimented by dissolving trehalose under heating conditions in water in an amount of 1.5, 2.0, 2.5, 2.8 or 3.3-times the water solubility at 10° C., dissolving in the solution other oligosaccharides having a trehalose structure within their molecules in an amount of 10, 30 or 60% to the trehalose, d.s.b, and allowing the resultant solution to stand at a relatively-low temperature.

Based on the results in Experiment 1, 1.5, 2.0, 2.5, 2.8 and 3.3-times the water solubility of trehalose in 100 parts by weight of water at 10° C. water corresponded to 83, 111, 138, 155 and 182 parts by weight of trehalose anhydride, d.s.b., respectively With this relationship, testing solutions with the composition as shown in Table 3 were prepared by dissolving under heating conditions in a respective glass beaker 100 parts by weight of water, trehalose in a prescribed part by weight, and either monoglucosyltrehalose, i.e., α-glucosyltrehalose or diglucosyltrehalose, i.e., α-maltosyltrehalose in a prescribed ratio, allowing the solution to stand in a thermostatic place kept at 5, 10 or 15° C. for checking the trehalose crystallization inhibitory effect. The results were in Table 3:

TABLE 3

| A | B | C | D | 5° C. | 10° C. | 15° C. |
|---|---|---|---|-------|--------|--------|
|   |   |   |   | 1.7** | 1.5**  | 1.3**  |
| 100 | 83 | 0 | 0 | + | + | + |
|   |   | 8.3 | 0 | - | - | - |
|   |   | 25 | 0 | - | - | - |
|   |   | 50 | 0 | - | - | - |
|   |   | 0 | 8.3 | - | - | - |
|   |   | 0 | 25 | - | - | - |
|   |   | 0 | 50 | - | - | - |
|   |   |   |   | 2.2** | 2.0** | 1.8** |
|   | 111 | 0 | 0 | + | + | + |
|   |   | 11 | 0 | + | - | - |
|   |   | 33 | 0 | - | - | - |
|   |   | 66 | 0 | - | - | - |
|   |   | 0 | 11 | - | - | - |
|   |   | 0 | 33 | - | - | - |
|   |   | 66 | 0 | - | - | - |
|   |   | 0 | 11 | - | - | - |
|   |   | 0 | 33 | - | - | - |
|   |   | 0 | 66 | - | - | - |
|   |   |   |   | 2.8** | 2.5** | 2.2** |
| 100 | 138 | 0 | 0 | + | + | + |
|   |   | 14 | 0 | + | + | - |
|   |   | 42 | 0 | + | + | - |
|   |   | 83 | 0 | + | + | - |
|   |   | 0 | 14 | + | - | - |
|   |   | 0 | 42 | + | - | - |
|   |   | 0 | 83 | - | - | - |
|   |   |   |   | 3.1** | 2.8** | 2.5** |
|   | 155 | 0 | 0 | + | + | + |
|   |   | 16 | 0 | + | + | + |
|   |   | 46 | 0 | + | + | + |
|   |   | 93 | 0 | + | + | + |
|   |   | 0 | 16 | + | + | - |
|   |   | 0 | 46 | + | + | - |
|   |   | 0 | 93 | + | - | - |
|   |   |   |   | 3.7** | 3.3** | 3.0** |
|   | 182 | 0 | 0 | + | + | + |
|   |   | 18 | 0 | + | + | + |
|   |   | 55 | 0 | + | + | + |
|   |   | 110 | 0 | + | + | + |
|   |   | 0 | 18 | + | + | + |
|   |   | 0 | 55 | + | + | + |
|   |   | 0 | 110 | + | + | + |

Note)
"*": "+" means that it crystallized and "-" means that it did not.
"**": Each value means a number to be multiplied with respect to the solubility of trehalose at each temperature.
"A": Water content in part by weight
"B": Trehalose content in part by weight
"C": Monoglucosyltrehalose
"D": Diglucosyltrehalose As evident from the results in Table 3, it was revealed that among other oligosaccharides having a trehalose structure within their molecules, mono- and di-glucosyltrehaloses showed a satisfactory trehalose crystallization inhibitory effect, particularly, diglucosyltrehalose showed a stronger effect. Even in the case of coexisting diglucosyltrehalose, the crystallization of trehalose was observed when trehalose was dissolved in water in an amount that exceeds 2.8-times the water solubility or 3.0-times the water solubility.

EXPERIMENT 4
Influence of Moisture Content on Bacterial Contamination of Syrups Containing Trehalose Over the Water Solubility A high trehalose content syrup, containing trehalose and other saccharides having a trehalose structure within their molecules, was used for checking the influence of moisture content on bacterial contamination and trehalose crystallization inhibitory effect. As shown in Table 4, testing solutions were prepared by dissolving under heating conditions monoglucosyl-trehalose, i.e., α-glucosyltrehalose and diglucosyltrehalose, i.e., α-maltosyltrehalose in aqueous trehalose solutions, which had been prepared by dissolving by heating trehalose in 100 parts by weight of water in an amount of 1.3–4.0 times the water solubility at 15° C., into trehalose syrups with a moisture content of 20–40 w/w %. The syrups were respectively placed in glass beakers and allowed to stand at 15° C. for two months for macroscopically checking both the formation of trehalose crystal and bacterial contamination grown on the syrups' surfaces.

TABLE 4

| Composition (part by weight) | | | | | | | |
|---|---|---|---|---|---|---|---|
| | Water | 100 | 100 | 100 | 100 | 100 | 100 |
| | (Moisture content (%) of syrup) | (20) | (25) | (28) | (31) | (35) | (40) |
| | Trehalose | 250 | 173 | 150 | 122 | 100 | 78 |
| | (Number to be multiplied with respect to the water solubility) | (4.0) | (2.8) | (2.4) | (2.0) | (1.6) | (1.3) |
| | (Trehalose (%) in syrup) | (50) | (44) | (42) | (38) | (35) | (31) |
| | Monoglucosyltrehalose | 15 | 15 | 15 | 15 | 15 | 15 |
| | Diglucosyltrehalose | 135 | 105 | 92 | 85 | 71 | 57 |
| Bacterial contamination* | | - | - | - | - | - | + |
| Formation of trehalose crystal** | | + | - | - | - | - | - |

Note) "*": "+" means that bacterial contamination was found and "-" means that no bacterial contamination was found.
"**": "+" means that it crystallized and "-" means that it did not crystallize.

As evident from the results in Table 4, the trehalose crystallization in the high trehalose content syrups according to the present invention were satisfactorily prevented, and it was revealed that no trehalose crystallization was observed in syrups dissolving trehalose in an amount up to about 2.8-times the water solubility, and that the present syrups with a moisture content of 35 w/w % or less are stable at ambient temperature and free of bacterial contamination.

The followings are the preferred examples of the present invention. Examples A and B describe the present high trehalose content syrups and the compositions using the same:

EXAMPLE A-1

Calcium carbonate was added to 33 w/v % corn starch suspension to give a final concentration of 0.1 w/w %, and the suspension was adjusted to pH 6.5, admixed with 0.2% per g starch of "TERRAMYL 60L", an α-amylase specimen commercialized by Novo Industri A/S Copenhagen, Denmark, and subjected to an enzymatic reaction at 95° C. for 15 min. The reaction mixture was heated by an autoclave at 120° C. for 10 min, then cooled to 45° C., and successively admixed with 5 units/g starch of a maltotetraose-forming enzyme, commercialized by Hayashibara Biochemical Laboratories, Inc., Okayama, Japan, as disclosed in Japanese Patent Kokoku No.89,916/95, 1,000 units/g starch of an isoamylase commercialized by the Hayashibara Biochemical Laboratories, Inc., and 5 units/g starch of a non-reducing saccharide-forming enzyme as disclosed in Japanese Patent Kokai No.143,876/95, followed by adjusting and enzymatically reacting the mixture to pH 6.0 and at 45° C. for 48 hours. The reaction mixture was heated at 95° C. for 10 min to inactivate the remaining enzyme, cooled, and filtered. The resulting filtrate was in a conventional manner decolored with activated charcoals, desalted, and purified with ion exchangers in H- and OH-form, and concentrated to obtain a syrup with a moisture content of about 30 w/w % in a yield of about 90%, d.s.b. The syrup had a DE of about 15 and contained about 2% α-glucosyltrehalose and about 60% α-maltosyltrehalose, d.s.b., and it can be arbitrarily used as a crystallization inhibitory agent for trehalose.

Fifty parts by weight of the syrup, 39 parts by weight of "TREHAOSE®", a crystalline trehalose hydrate commercialized by Hayashibara Shoji, Inc., Okayama, Japan, and 11 parts by weight of water were dissolved by heating into a high trehalose content syrup with a moisture content of about 30 w/w % and a DE of about 8. The product is a relatively-low DE, viscous and sweet syrup which contains trehalose in an amount of about 1.9-times the water solubility of trehalose at 15° C., and about 62% other oligosaccharides, having a trehalose structure within their molecules, to the trehalose content, d.s.b. Although the syrup is a supersaturated solution, it is well prevented from crystallizing trehalose, stable at ambient temperature, and easily handled, and it can be arbitrarily used as a sweetener, taste-improving agent, quality-improving agent, or base for pulverization in food products, cosmetics, and pharmaceuticals.

EXAMPLE A-2

A saccharide solution, as a feed, containing α-glucosyltrehalose and α-maltosyltrehalose, obtained by the method in Example A-1, was column chromatographed using a column packed with "XT-1016 (Na-form, polymerization degree of 4%)", an alkaline metal strong-acid cation exchanger commercialized by Tokyo Organic Chemical Industries, Ltd., Tokyo, Japan. The resin was packed in four jacketed stainless steel columns with an inner diameter of 5.4 cm, and the columns were cascaded in series to give a total gel-bed depth of about 20 m. While keeping the inner column temperature at 55° C., 5 v/v % of the saccharide solution was fed to the resin and fractionated by feeding to the columns water heated to 55° C. at an SV (space velocity) 0.13. Fractions rich in mono- and di-saccharides were removed, while those rich in α-maltosyltrehalose were collected, purified, and concentrated into a syrup with a moisture content of about 30 w/w %. The product had a DE of about 9 and contained about 65% α-maltosyltrehalose, d.s.b., and it can be arbitrarily sued as a crystallization preventing agent for trehalose.

Forty parts by weight of the syrup was mixed with 46 parts by weight of crystalline trehalose hydrate and 14 parts by weight of water, and the mixture was dissolved by heating into a high trehalose content syrup with a moisture content of about 30 w/w % and a DE of about 4. The product is a syrup with a relatively-low DE, viscosity, and sweetness, which dissolves trehalose in an amount of about 2.3-times the water solubility at 15° C. and contains about 45% of other oligosaccharides, having a trehalose structure within their molecules, to the trehalose, d.s.b. Although the product is a supersaturated solution of trehalose, the crystallization of trehalose is satisfactorily prevented, stable at ambient temperature, and easily handled. Therefore, it can be arbitrarily used as a sweetener, taste-improving agent, quality-improving agent, or base for pulverization in food products, cosmetics, and pharmaceuticals.

EXAMPLE A-3

In Example A-1, the reaction mixture, after heated at 95° C. for 10 min to inactivate the remaining enzyme, was further mixed with 2 units of "β-AMYLASE #15", a β-amylase specimen commercialized by Nagase Biochemicals, Ltd., Kyoto, Japan, followed by an enzymatic reaction at 50° C. for 20 hours. The reaction mixture thus obtained was heated to inactivate the remaining enzyme, and in a conventional manner decolored, desalted, and purified, followed by concentrating the purified solution to obtain a syrup with a moisture content of about 60 w/w % in a yield of about 90%, d.s.b. To increase the content of diglucosyltrehaloses, the syrup as a feed was chromatographed according to the method in Example A-2 except that "DOWEX 50W-X4 ($Ca^{++}$-form)", an alkaline strong-acid cation exchange resin commercialized by Dow Chemical Co., Midland, Mich., USA, was used to obtain a fraction rich in diglucosyltrehaloses, followed by purifying and concentrating the fraction into a syrup with a moisture content of about 30 w/w %. The syrup had a DE of about one and contained about 90%, d.s.b., of diglucosyl-trehaloses such as α-maltosyltrehalose, and it can be arbitrarily used as a crystallization preventing agent for trehalose.

To 35 parts by weight of the syrup were added 50 parts by weight of crystalline trehalose hydrate and 15 parts by weight of water, and the mixture was dissolved by heating into a high trehalose content syrup with a DE of one or lower and a moisture content of 30 w/w %. The product is a relatively-low DE, viscous and sweet syrup which dissolves trehalose in an amount of about 2.4-times the water solubility at 15° C., and contains about 50% of other oligosaccharides, having a trehalose structure within their molecules and containing α-maltosyltrehalose as a main ingredient, to the trehalose, d.s.b. Although the product is a supersaturated solution of trehalose, the crystallization of trehalose is satisfactorily prevented, stable at ambient temperature, and easily handled. Therefore, it can be arbitrarily used as a sweetener, taste-improving agent, quality-improving agent, or base for pulverization in unfood products, cosmetics, and pharmaceuticals.

EXAMPLE A-4

Calcium carbonate was added to 30 w/v % corn starch suspension to give a final concentration of 0.1 w/w %, and the mixture was adjusted to pH 6.5, mixed with 0.2 w/w % per g starch of "TERMAMYL 60L", an α-amylase specimen commercialized by Novo Industri A/S Copenhagen, Denmark, and subjected to an enzymatic reaction at 95° C. for 15 min. The reaction mixture was autoclaved at 120° C. for 10 min, cooled to 45° C., mixed with one unit/g starch of "NEO-SPITASE", an α-amylase specimen commercialized by Nagase Biochemicals, Ltd., Kyoto, Japan, 1,000 units of isoamylase, 5 units/g starch of a non-reducing saccharide-forming enzyme as disclosed in Japanese Patent Kokai No.143,786/95, then adjusted to pH 6.0, and reacted at 45° C. for 48 hours. The reaction mixture thus obtained was heated to inactivate the remaining enzyme, and in a conventional manner decolored, desalted, purified, and concentrated to obtain a syrup with a moisture content of about 30 w/w % in a yield of about 90%, d.s.b. The syrup had a DE of about 11 and contained about 5% α-glucosyltrehalose and about 12% α-maltosyltrehalose, d.s.b. The product can be arbitrarily used as a crystallization preventing agent for trehalose.

To 50 parts by weight of the syrup were added 38 parts by weight of crystalline trehalose hydrate and 12 parts by weight of water, and the mixture was dissolved by heating into a high trehalose content syrup with a DE of about 6 and a moisture content of about 30 w/w %. The product had a relatively-low DE, viscosity, and sweetness, dissolved trehalose in an amount of about 1.9-times the water solubility of trehalose at 15° C., and contained about 58% of other oligosaccharides, having a trehalose structure within their molecules, to the trehalose, d.s.b. Although the product is a supersaturated solution of trehalose, it is satisfactorily prevented from crystallizing trehalose, stable at ambient temperature, and easily handled. Therefore, the product can be arbitrarily used as a sweetener, taste-improving agent, quality-improving agent, or base for pulverization in food products, cosmetics, and pharmaceuticals.

EXAMPLE A-5

Corn starch was prepared into a 10 w/v % suspension which was then contacted with α-amylase into a liquefied solution. To the resulting solution were added 3 units/g starch of a non-reducing saccharide-forming enzyme as disclosed in Japanese Patent Kokai No.213,283/95, 5 units/g starch of a trehalose-releasing enzyme, 1,000 units/g starch of isoamylase, and one unit/g starch of a maltotetraose-forming enzyme, adjusted to pH 6.0, and subjected to an enzymatic reaction at 40° C. for 48 hours. The reaction mixture was heated to inactivate the remaining enzyme, and in a conventional manner decolored, desalted, purified, and concentrated to obtain a syrup with a moisture content of about 30 w/w % and a DE of about 15 in a yield of about 90%, d.s.b. The product is a relatively-low viscous and sweet syrup which dissolves trehalose in an amount of about 1.9-times the water solubility of trehalose at 15° C. and contains about 30% of other oligosaccharides, having a trehalose structure within their molecules, to the trehalose, d.s.b. Although the product is a supersaturated solution of trehalose, it is satisfactorily prevented from crystallizing trehalose, stable at ambient temperature, and easily handled. Therefore, the product can be arbitrarily used as a sweetener, taste-improving agent, quality-improving agent, or base for pulverization in food products, cosmetics, and pharmaceuticals.

EXAMPLE A-6

A high trehalose content syrup, obtained by the method in Example A-5, was placed in an autoclave, admixed with 10% Raney nickel, heated to a temperature of 90–120° C. under stirring conditions, and completed the hydrogenation by increasing the hydrogen pressure to 20–120 kgf/cm$^2$. Thereafter, the Raney nickel was removed and in a conventional manner decolored, desalted, purified, and concentrated to obtain a syrup with a moisture content of about 30 w/w % in a yield of about 90%, d.s.b. The product dissolves trehalose in an amount of about 1.9-times the water solubility at 15° C. and contains about 30% of other oligosaccharides, having a trehalose structure within their molecules, to the trehalose, d.s.b. Although the product is a supersaturated solution of trehalose, it is satisfactorily prevented from crystallizing trehalose, substantially free from reducibility, relatively-highly stable, and easily handled. Therefore, the product can be arbitrarily used as a sweetener, taste-improving agent, quality-improving agent, low dental-carries-inducing sweetener, and low-caloric sweetener in food products, cosmetics, and pharmaceuticals.

EXAMPLE A-7

Calcium carbonate was added to 30 w/v % corn starch suspension to give a final concentration of 0.1 w/w %, and the mixture was adjusted to pH 6.5, mixed with 0.2 w/w % per g starch of "TERMAMYL 60L", an α-amylase specimen commercialized by Novo Industri A/S Copenhagen, Denmark, and subjected to an enzymatic reaction at 95° C. for 15 min. The reaction mixture was autoclaved at 120° C. for 10 min, cooled to 45° C., mixed with one unit/g starch of "NEO-SPITASE", an α-amylase specimen commercialized by Nagase Biochemicals, Ltd., Kyoto, Japan, 5 units/g starch of a non-reducing saccharide-forming enzyme as disclosed in Japanese Patent Kokai No.143,786/95, then adjusted to pH 6.0, and reacted at 45° C. for 48 hours. The reaction mixture thus obtained was heated to inactivate the remaining enzyme, and in a conventional manner decolored, desalted, purified, and concentrated to obtain a syrup with a moisture content of about 30 w/w % in a yield of about 90%, d.s.b. The syrup had a DE of about 8 and contained about 4% α-glucosyltrehalose and about 7% α-maltosyltrehalose, d.s.b. The product can be arbitrarily used as a crystallization preventing agent for trehalose.

To 55 parts by weight of the syrup were added 35 parts by weight of crystalline trehalose hydrate and 10 parts by weight of water, and the mixture was dissolved by heating into a high trehalose content syrup with a DE of about 5 and a moisture content of about 30 w/w %. The product had a relatively-low DE and sweetness and a relatively-high viscosity, dissolved trehalose in an amount of about 1.7-times the water solubility at 15° C., and contained about 20% of other oligosaccharides, having a trehalose structure within their molecules, to the trehalose, d.s.b. Although the product is a supersaturated solution of trehalose, it is satisfactorily prevented from crystallizing trehalose, stable at ambient temperature, and easily handled. Therefore, the product can be arbitrarily used as a sweetener, taste-improving agent, quality-improving agent, or base for pulverization in food products, cosmetics, and pharmaceuticals.

EXAMPLE B-1

Beverage Containing Lactic Acid Bacteria

One hundred and seventy-five parts by weight of skim milk and 150 parts by weight of a high trehalose content syrup, obtained by the method in Example A-5, were dissolved in 1,200 parts by weight of water, and the solution was sterilized at 65° C. for 30 min, cooled to 40° C. and in a conventional manner inoculated with 30 parts by weight of a starter and incubated at 37° C. for 8 hours to obtain a beverage which contained lactic acid bacteria, had a satisfactory flavor and taste. The product stably keeps the bacteria and satisfactorily promotes the growth of bifid bacteria because it contains oligosaccharides.

EXAMPLE B-2

Coffee

One hundred parts by weight of roasted coffee beans was pulverized and extracted with 1,000 parts by weight of hot water to obtain an about 860 parts by weight of a coffee extract. About 450 parts by weight of the extract was admixed to homogeneity with about 150 parts by weight of a high trehalose content syrup, obtained by the method in Example A-3, and about 400 parts by weight of water containing an adequate amount of sodium hydrogen carbonate into a coffee with a pH of about 7. The coffee was in a conventional manner distributed into cans which were then heated at 120° C. for 30 min to obtain a caned coffee. The product is a high-quality coffee with a satisfactory flavor and taste. After standing in an automatic vending machine at 60° C. for one month, it retained the flavor and taste. When tasted after cooling during summer, it is still be a high quality coffee with the high quality flavor and taste.

EXAMPLE B-3

Trehalose-Enriched Beverage

To 695 parts by weight of a high trehalose content syrup, obtained by the method in Example A-7, were added 3 parts by weight of citric acid, an adequate amount of a grape fruit flavor, 100 parts by weight of an aqueous mineral/vitamin solution consisting of 0.015% calcium lactate, 0.025% potassium chloride, 0.009% magnesium chloride, heptahydrate, 0.122% monosodium glutamate, 0.3% L-ascorbic acid, 0.002% thiamine, 0.001% riboflavine, 0.002% pyridoxine, and water. The mixture was volumed up with water up to give a total volume of 1,000 parts by weight which was then in a conventional manner injected into a can, and sterilized by heating to obtain an energy-supplementing beverage. The product, containing saccharides including trehalose in an amount of as much as about 50%, is an easily swallowable, low-sweet, adequately-viscous, beverage, which can be satisfactorily used as an emergency ration and easily usable energy-supplementing beverage used just before or during sports and physical exercises.

EXAMPLE B-4

Hard Candy

One hundred parts by weight of a high trehalose content syrup, obtained by the method in Example A-1, was concentrated by heating under a reduced pressure to lower the moisture content up to below 2 w/w %. The concentrate was mixed with 0.5 part by weight of citric acid and adequate amounts of a lemon flavor and coloring agent, and the mixture was in a conventional manner shaped into the desired product. The product is a high quality hard candy with a satisfactory biting property and taste, and free from crystallizing saccharides and changing the shape.

EXAMPLE B-5

An (processed beans)

Ten parts by weight of material adzuki beans was in a conventional manner mixed with water and boiled to remove bitterness and ash taste, followed by removing water-soluble impurities to obtain about 21 parts by weight of adzuki-tsubuan, processed adzuki beans which keep their shape. To the product were added 14 parts by weight of sucrose, 5 parts by weight of a high trehalose content syrup obtained by the method in Example A-2, and 4 parts by weight of water, and the mixture was boiled, mixed with a small amount of salad oil, and kneaded up while keeping attention not to paste the beans to obtain about 35 parts by weight of the desired product. The product has no burned color but has a satisfactory biting property, flavor and taste, and it can be suitably used as a material for bean-jam buns, "manju" (a bun with a bean-jam filling), "dango" (a dumpling), "monaka" (a bean-jam-filled wafer), ice creams, and sherbets.

EXAMPLE B-6

Strawberry Jam

Fifteen parts by weight of a fresh strawberries, 6 parts by weight of sucrose, 2 parts by weight of maltose, 4 parts by weight of a high trehalose content syrup obtained by the method in Example A-2, 0.05 part by weight of pectin, and 0.01 part by weight of citric acid were placed in a pan and boiled up into a jam, followed by bottling the jam. The product is a high quality jam with a satisfactory flavor, taste, and color.

EXAMPLE B-7

Bun

One hundred parts by weight of wheat flour, 2 parts by weight of a yeast, 5 parts by weight of sugar, 2 parts by weight of a high trehalose content syrup obtained by the method in Example A-4, and 0.1 part by weight of yeast food were in a conventional manner kneaded with water and incubated at 26° C. for 2 hours to ferment the yeast, followed by aging for 30 min and baking up. The resulting product is a high quality bun with a satisfactory color and texture, adequate elasticity, and mild sweetness.

EXAMPLE B-8

Custard Cream

One hundred parts by weight of corn starch, 100 parts by weight of a high trehalose content syrup obtained by the method in Example A-1, 80 parts by weight of maltose, 20 parts by weight of sucrose, and one part by weight of salt were sufficiently mixed, then admixed with 280 parts by weight of fresh eggs, gradually mixed with 1,000 parts by weight of milk, and heated under stirring conditions. The heating was suspended when the whole contents were gelatinized to show semitransparency, and the mixture was cooled, mixed with an adequate amount of a vanilla flavor, weighed, injected, and packed into the desired product. The product has a smooth gloss and a mild sweetness and taste, and has a relatively-long shelf life because the retrogradation of the gelatinized starch is well prevented

EXAMPLE B-9

Gyuhi (starch paste)

Four parts by weight of glutinous rice starch was suspended in 6 parts by weight of water, and the suspension was placed in a crate with a spread wet-cloth, steamed up at 100° C. for 20 min, mixed with 6 parts by weight of a high trehalose content syrup obtained by the method in Example A-1, and 2 parts by weight of sugar were sufficiently kneaded, followed by shaping the mixture into a gyuhi. The product has a satisfactory taste and flavor. The retrogradation of the gelatinized starch is well prevented, and this satisfactorily prolongs the shelf life.

EXAMPLE B-10

Icing

Eighty parts by weight of a high trehalose content syrup, obtained by the method in Example A-2, was mixed while heating with 1.2 parts by weight of an emulsifier (a sugar ester), and further mixed with 107 parts by weight of "TREHAOSE®", a crystalline trehalose hydrate product commercialized by Hayashibara Shoji, Inc., Okayama, Japan, followed by mixing with 7.5 parts by weight of oil and fat at 45° C. to obtain an icing. The product contains a fine trehalose crystal and has a satisfactory formability free of stickiness and a relatively-long shelf life.

EXAMPLE B-11

Soft Candy

Sixty parts by weight of a high trehalose content syrup, obtained by the method in Example A-4, and 180 parts by weight of crystalline trehalose hydrate were mixed and concentrated by heating, and the concentrate was admixed with 15 parts by weight of 20 w/v % pullulan solution and 60 parts by weight of 10 w/v % agar solution and concentrated by heating. The resulting concentrate was mixed with 70 parts by weight of milk cream, 120 parts by weight of skim milk, 1.5 parts by weight of sugar ester, and 40 parts by weight of margarine, followed by concentrating by heating up to give a Brix 85. The mixture thus obtained was in a conventional manner shaped into a soft candy which contains a fine trehalose crystal, has an enriched milk-flavor, and has substantially no stickiness to the teeth. Because it does not contain sugar, it is a health candy with less fear of causing dental carries.

EXAMPLE B-12

Bonbon

Five parts by weight of a high trehalose content syrup obtained by the method in Example A-5, 300 parts by weight of crystalline trehalose hydrate, and 115 parts by weight of water were mixed, and the mixture was boiled by heating up to give a Brix 70, cooled to 80° C., admixed with 40 parts by weight of a brandy, and shaped into a bonbon in a conventional manner. The product is a high-quality bonbon which contains a fine trehalose crystal, has an enriched brandy-flavor, and less deteriorates during storage.

EXAMPLE B-13

Ham

Fifteen parts by weight of salt and 3 parts by weight of potassium nitrate were added to 1,000 parts by weight of hams and homogeneously ground them together, followed by piling and standing them in a relatively-cold place overnight. The resulting hams were soaked for a week in a salt solution, consisting of 440 parts by weight of water, 100 parts by weight of salt, 3 parts by weight of potassium nitrate, an adequate amount of spices, and 60 parts by weight of a high trehalose content syrup obtained by the method in Example A-3, and in a conventional manner washed with water, tied round, smoked, cocked, cooled, and packed to obtain the desired product. The product was a well colored, enriched flavor and color, high-quality ham.

EXAMPLE B-14

Tsukudani (food boiled down in soy)

Two hundred and fifty parts by weight of tangle, which had been removed sand, acid-treated and cut into cubes which were then mixed with 212 parts by weight of soy, 318 parts by weight of an amino acid solution, 70 parts by weight of a high trehalose content syrup obtained by the method in Example A-1, and 20 parts by weight of sucrose, further mixed while boiling with 12 parts by weight of sodium glutamate and 8 parts by weight of caramel, and boiled up into the desired product. The product is a less dental-carries-inducing tsukudani which has a satisfactory taste, flavor, and gloss, and stimulates your appetite.

EXAMPLE B-15

Cosmetic Cream

Two parts by weight of polyoxyethylene glycol monostearate, 5 parts by weight of self-emulsifying glycerine monostearate, 2 parts by weight of a high trehalose content syrup obtained by the method in Example A-3, one part by weight of α-glycosylrutin, one part by weight of liquid paraffine, 10 parts by weight of glyceryl trioctanoate, and an adequate amount of an antiseptic were dissolved by heating in a conventional manner. The resulting solution was mixed with 2 parts by weight of L-lactic acid, 5 parts by weight of 1,3-butylene glycol, and 66 parts by weight of refined water, and the mixture was emulsified by a homogenizer, followed by the addition of an adequate amount of a flavor and mixing by stirring to obtain a cosmetic cream. Since the product has an effective antioxidation activity and satisfactory stability, it can be arbitrarily used as a sun-screening, skin-refining or skin-whitening.

EXAMPLE B-16

| Toothpaste | |
| --- | --- |
| Composition | Part by weight |
| Dicalcium hydrogenphosphate | 45.0 |
| Pullulan | 2.95 |
| Sodium lauryl sulfate | 1.5 |
| Glycerine | 20.0 |
| Polyoxyethylene sorbitan laurate | 0.5 |
| Antiseptic | 0.05 |
| A high trehalose content syrup obtained by the method in Example A-6 | 12.0 |
| Maltitol | 5.0 |
| Water | 13.0 |

The ingredients in the composition were in a conventional manner mixed into a toothpaste. The product has a moderate sweetness, and it can be specifically used for children.

EXAMPLE B-17

Ointment for Trauma

Two hundred parts by weight of a high trehalose content syrup obtained by the method in Example A-3 and 360 parts by weight of maltose were admixed with 50 parts by weight of methanol which dissolved 3 parts by weight of iodine, and further mixed with 140 parts by weight of 14 w/v % aqueous pullulan solution to obtain an ointment for trauma with a satisfactory adhesiveness. Since the product exerts an effective antiseptic activity due to iodine and acts as an energy-supplement agent for living cells due to trehalose and maltose, it shortens the healing period and cures completely the wounded sites.

EXAMPLE B-18

Nutrition for Intubation Feeding

A composition, consisting of 20 parts by weight of a high trehalose content powder prepared by drying by spraying a high trehalose content syrup obtained by the method in Example A-2, 1.1 parts by weight of glycine, 0.4 part by weight of sodium glutamate, 0.4 part by weight of calcium lactate, 0.1 part by weight of magnesium carbonate, 0.01 part by weight of thiamine, and 0.01 part by weight of riboflavin, was prepared. Twenty-four g aliquots of the composition were injected into aluminum laminated small-bags and heat sealed to obtain the desired product. One bag of the product is dissolved in about 33–500 ml water into a nutrient supplementing agent, then administered to the nasal cavity, stomach, and intestines. The product can be arbitrarily used as a parenteral, supplemental nutrition for humans and domestic animals.

EXAMPLE B-19

Interferon Liquid

A natural human interferon-γ preparation, produced by Hayashibara Biochemical Laboratories, Inc., Okayama, Japan, and commercialized by Cosmo Bio Co., Ltd., Tokyo, Japan, was in a conventional manner fed to a column of an immobilized anti-human interferon-γ antibody to adsorb the interferon, followed by passing calf serum albumin as a stabilizer through the column, removing the excessive amount of the albumin, altering the pH, and eluting the interferon by feeding a physiological saline containing 7%, d.s.b., of a high trehalose content syrup obtained by the method in Example A-3. The eluate was membrane filtered and aseptically injected into vials containing $10^5$ units/ml of the interferon. The product can be arbitrarily used by orally or parenterally administering to humans at a dose of 1–20 ml/adult/day for the treatment of viral diseases, allergic diseases, rheumatisms, diabetics, and malignant tumors. The trehalose and diglucosyltrehalose such as α-maltosyltrehalose contained in the product act as stabilizers for the interferon to stably retain the activity even after standing at 4° C. or 25° C. for 20 days.

As evident from the above, the present invention provides a high trehalose content syrup which is stabilized, free of or substantially free of crystallization at ambient temperature, and substantially free from bacterial contamination. Unlike conventional crystalline trehalose powders, the present syrup requires no dissolving step, and it can be easily handled, tank-stored, pump-transported and transported by tank trucks. Comparing conventional amylaceous saccharides, the syrup is a novel-type of syrup which has a relatively-low DE and viscosity and a high-level sweetness, and which can be arbitrarily used as a sweetener, taste-improving agent, quality-improving agent, and base for pulverization in the production of food products, cosmetics, and pharmaceuticals.

Thus, the establishment of the present invention provides a high trehalose content syrup, with a satisfactory stability at ambient temperature, which has been required but not yet obtained, and the invention will unfathomable effect on the fields of food, cosmetic, and pharmaceutical industries.

While there has been described what is at present considered to be the preferred embodiments of the invention, it will be understood the various modifications may be made therein, and it is intended to cover in the appended claims all such modifications as fall within the true spirit and scope of the invention.

We claim:

1. A non- or substantially non-crystalline high trehalose content syrup, which has a supersaturated content of trehalose in water and which further comprises a stabilizing-effective amount of another dissolved oligosaccharide having a trehalose structure within the molecule.

2. The syrup of claim 1 wherein solubility of trehalose is up to about 2.8-times greater than the solubility of trehalose in water.

3. The syrup of claim 1, which contains not higher than 35 w/w % moisture.

4. The syrup of claim 1, which contains at least 10 w/w % of said another oligosaccharide to said trehalose, on a dry solid basis.

5. The syrup of claim 1, wherein said another oligosaccharide is one or more members selected from the group consisting of monoglucosyltrehalose, diglucosyltrehalose, and triglucosyltrehalose.

6. The syrup of claim 1, which does not or substantially does not crystallize at 15° C.

7. A composition which contains at least 0.5 w/w % of said syrup of claim 1 together with at least one other component suitable for incorporation in a food product, cosmetic or pharmaceutical composition.

8. The composition of claim 7, which is in the form of a food product, cosmetic, or pharmaceutical.

9. A method for preventing the crystallization of trehalose, which comprises incorporating in a trehalose syrup a stabilizing-effective amount of another oligosaccharide having a trehalose structure within the molecule.

10. The method of claim 9, wherein the content of said another oligosaccharide to be coexisted is at least 10 w/w % to said trehalose, on a dry solid basis.

11. The method of claim 9, wherein said another oligosaccharide is one or more members selected from the group consisting of monoglucosyltrehalose, diglucosyltrehalose, and triglucosyltrehalose.

12. The syrup of claim 1 wherein said stabilizing-effective amount of another dissolved oligosaccharide having a trehalose structure within the molecule is at least 10 w/w % to said trehalose on a dry solid basis.

13. The method of claim 9 wherein said trehalose syrup has a water content not higher than 35 w/w %.

14. A process for producing a non- or substantially non-crystalline high trehalose content syrup, which comprises providing a solution of water, an amount of trehalose relative to said water in which said trehalose is supersaturated, and a stabilizing-effective amount of another oligosaccharide having a trehalose structure within the molecule.

15. A process according to claim 14, wherein said solution is obtained by dissolving trehalose in water in an amount that exceeds the water solubility by heating a mixture of water and trehalose, and then incorporating said other oligosaccharide having a trehalose structure within the molecule into the heated trehalose solution.

16. A process according to claim 14, comprising preparing a supersaturated solution of trehalose and mixing said supersaturated solution with a high-concentration solution of said other oligosaccharide having a trehalose structure within the molecule.

17. The process of claim 14, comprising dissolving said trehalose in an amount of said water up to about 2.8-times its water solubility.

18. The process of claim 14, comprising using an amount of water to provide said syrup with a moisture content not greater than 35 w/w %.

19. The process of claim 14, comprising using an amount of said another oligosaccharide in an amount to provide said syrup with a content of said another oligosaccharide of at least 10 w/w % with respect to said trehalose, on a dry solid basis.

20. The process of claim 14, wherein said another oligosaccharide is selected from the group consisting of monoglucosyltrehalose, diglucosyltrehalose, and triglucosyltrehalose.

21. The process of claim 14, wherein said high trehalose content syrup produced does not or substantially does not crystallize at 15° C.

* * * * *